(12) United States Patent
Nilsson et al.

(10) Patent No.: US 9,234,206 B2
(45) Date of Patent: Jan. 12, 2016

(54) MODULATION OF FLOWERING TIME AND GROWTH CESSATION IN HARDWOOD TREES

(75) Inventors: Ove Nilsson, Umea (SE); Henrik Bohlenius, Umea (SE)

(73) Assignee: Swetree Technologies AB, Umea (SE)

( * ) Notice: Subject to any disclaimer, the term of this patent is extended or adjusted under 35 U.S.C. 154(b) by 1733 days.

(21) Appl. No.: 11/575,563

(22) PCT Filed: Sep. 20, 2005

(86) PCT No.: PCT/IB2005/003106
§ 371 (c)(1),
(2), (4) Date: Mar. 19, 2007

(87) PCT Pub. No.: WO2006/033014
PCT Pub. Date: Mar. 30, 2006

(65) Prior Publication Data
US 2008/0066198 A1    Mar. 13, 2008

(30) Foreign Application Priority Data
Sep. 20, 2004 (GB) .................................. 0420874.0

(51) Int. Cl.
*C12N 15/82* (2006.01)
*C07K 14/415* (2006.01)

(52) U.S. Cl.
CPC ............ *C12N 15/827* (2013.01); *C07K 14/415* (2013.01); *C12N 15/8201* (2013.01)

(58) Field of Classification Search
USPC ........................................................ 800/298
See application file for complete search history.

(56) References Cited

U.S. PATENT DOCUMENTS 6,225,530 B1 *    5/2001  Weigel et al. ................. 800/290
2006/0070141 A1 *  3/2006  Nielsen et al. ................ 800/287

FOREIGN PATENT DOCUMENTS

WO    WO 02/44390      6/2002
WO    WO 2004/067723   8/2004

OTHER PUBLICATIONS

Igasaki et al (2004, NCBI Accession No. AB110009).*
BLAST alignment of SEQ ID No. 1; conducted Nov. 8, 2013 via http://blast.ncbi.nlm.nih.gov/Blast.cgi (results attached).*
Submission information for thesis labeled Exhibit B filed by Applicant Apr. 28, 2011; retrieved from http://pub.epsilon.slu.se/1584/ (results attached).*
Newton et al., Molecular phylogeography, intraspecific variation and the conservation of tree species, 14 TREE No. 4, 140-145 (1999)).*
Pnueli et al., Tomato SP-Interacting Proteins Define a Conserved Signaling System That Regulates Shoot Architecture and Flowering, 13 Plant Cell, 2687-2702 (2001)).*
GenBank Accession No. AB110009 (published Jun. 8, 2004; retrieved from http://www.ncbi.nlm.nih.gov/nuccore/AB110009 on Nov. 14, 2013).*
(Merkle et al., Harwood tree biotechnology, 41 In Vitro Cell Dev Biol Plant, 602-619 at 605 (2005)).*
Brunner et al., "Poplar homologs of genes controlling floral meristem identity and flowering time: expression over a seasonal cycle and a continuous age gradient," *Plant Biology*, 2000, 42; Abstract, Ann. Mtg. Am. Soc. Plant Pathologists, Jul. 15-19, 2000.
Brunner and Nilsson, "Revisiting tree maturation and floral initiation in the poplar functional genomics era," *New Phytologist* 164:43-51, 2004.
Kardailsky et al., "Activation Tagging of the Floral Inducer FT," *Science* 286:1962-1965, 1999.
Weigel and Nilsson, "A developmental switch sufficient for flower initiation in diverse plants," *Nature* 377:495-500, 1995.
XP-002367958; EMBL Database Accession No. EM_PRO: AB110009, "Populus nigra PnFT3c mRNA for flowering locus T, complete cds," *EBI* (Nov. 13, 2003) (1 page).
XP-002367959; EMBL Database Accession No. EM_PRO: AB109804, "Populus nigra PnFT2a mRNA for flowering locus T, complete cds," *EBI* (Nov. 11, 2003) (1 page).

* cited by examiner

*Primary Examiner* — Stuart F Baum
(74) *Attorney, Agent, or Firm* — Klarquist Sparkman, LLP

(57) ABSTRACT

This invention relates to the identification and characterization of poplar PFT genes and their role in the induction of early flowering and repression of short-day induced growth cessation in perennial plant species. This has important applications for forestry, for example in tree breeding programs.

16 Claims, 8 Drawing Sheets

Figure 1

Wild type         35S::PFT L-1

SEQUENCE LISTING

```
<160> NUMBER OF SEQ IDS NOS: 12

<210> SEQ ID NO 1
<211> LENGTH: 174
<212> TYPE: PRT
<213> ORGANISM: Populus trichocarpa

<400> SEQUENCE: 1

Met Ser Arg Asp Arg Asp Pro Leu Ser Val Gly Arg Val Ile Gly Asp
1               5                   10                  15

Val Leu Asp Pro Phe Thr Lys Ser Ile Ser Leu Arg Val Thr Tyr Ser
                20                  25                  30

Ser Arg Glu Val Asn Asn Gly Cys Glu Leu Lys Pro Ser Gln Val Ala
            35                  40                  45

Asn Gln Pro Arg Val Asp Ile Gly Gly Glu Asp Leu Arg Thr Phe Tyr
        50                  55                  60
```

```
Thr Leu Val Met Val Asp Pro Asp Ala Pro Ser Pro Ser Asp Pro Ser
 65                  70                  75                  80

Leu Arg Glu Tyr Leu His Trp Leu Val Thr Asp Ile Pro Ala Thr Thr
             85                  90                  95

Gly Ala Ser Phe Gly His Glu Thr Val Cys Tyr Glu Ser Pro Arg Pro
            100                 105                 110

Thr Met Gly Ile His Arg Phe Val Phe Val Leu Phe Arg Gln Leu Gly
        115                 120                 125

Arg Gln Thr Val Tyr Ala Pro Gly Trp Arg Gln Asn Phe Asn Thr Arg
    130                 135                 140

Asp Phe Ala Glu Val Tyr Asn Leu Gly Ser Pro Val Ala Ala Val Tyr
145                 150                 155                 160

Phe Asn Cys Gln Arg Glu Ser Gly Ser Gly Gly Arg Arg Arg
                165                 170

<210> SEQ ID NO 2
<211> LENGTH: 525
<212> TYPE: DNA
<213> ORGANISM: Populus trichocarpa

<400> SEQUENCE: 2
atgtcaaggg acagagatcc tctgagcgtt ggccgtgtta taggggacgt gctggacccc      60
ttcacaaagt ctatctccct cagggtcact tacagctcca gagaggtcaa caatggttgc     120
gagctcaagc cctctcaggt tgccaaccag cctagggttg atattggcgg ggaagatcta     180
aggaccttct acactctggt tatggtggac cctgatgcac ccagcccaag tgaccccagc     240
ctaagagaat atttgcattg gttggtgact gatattccag caacaactgg ggcaagcttt     300
ggccatgaaa ctgtgtgcta tgagagcccg aggccgacaa tgggaattca tcggtttgtt     360
ttcgtcttgt tcggcaact gggcaggcaa actgtgtatg cccctgggtg cgccagaac      420
ttcaacacca gagactttgc tgaggtctac aatcttggat cgccagtggc tgctgtttat     480
ttcaactgcc agagggagag tggctctggt ggtaggaggc gataa                    525

<210> SEQ ID NO 3
<211> LENGTH: 175
<212> TYPE: PRT
<213> ORGANISM: Arabidopsis thaliana

<400> SEQUENCE: 3

Met Ser Ile Asn Ile Arg Asp Pro Leu Ile Val Ser Arg Val Val Gly
  1               5                  10                  15

Asp Val Leu Asp Pro Phe Asn Arg Ser Ile Thr Leu Lys Val Thr Tyr
             20                  25                  30

Gly Gln Arg Glu Val Thr Asn Gly Leu Asp Leu Arg Pro Ser Gln Val
         35                  40                  45

Gln Asn Lys Pro Arg Val Glu Ile Gly Gly Glu Asp Leu Arg Asn Phe
     50                  55                  60

Tyr Thr Leu Val Met Val Asp Pro Asp Val Pro Ser Pro Ser Asn Pro
 65                  70                  75                  80

His Leu Arg Glu Tyr Leu His Trp Leu Val Thr Asp Ile Pro Ala Thr
             85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125
```

Gly Arg Gln Thr Val Tyr Ala Pro Gly Trp Arg Gln Asn Phe Asn Thr
            130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 4
<211> LENGTH: 175
<212> TYPE: PRT
<213> ORGANISM: Arabidopsis thaliana

<400> SEQUENCE: 4

Met Ser Leu Ser Arg Arg Asp Pro Leu Val Val Gly Ser Val Val Gly
1               5                   10                  15

Asp Val Leu Asp Pro Phe Thr Arg Leu Val Ser Leu Lys Val Thr Tyr
                20                  25                  30

Gly His Arg Glu Val Thr Asn Gly Leu Asp Leu Arg Pro Ser Gln Val
            35                  40                  45

Leu Asn Lys Pro Ile Val Glu Ile Gly Gly Asp Asp Phe Arg Asn Phe
        50                  55                  60

Tyr Thr Leu Val Met Val Asp Pro Asp Val Pro Ser Pro Ser Asn Pro
65                  70                  75                  80

His Gln Arg Glu Tyr Leu His Trp Leu Val Thr Asp Ile Pro Ala Thr
                85                  90                  95

Thr Gly Asn Ala Phe Gly Asn Glu Val Val Cys Tyr Glu Ser Pro Arg
            100                 105                 110

Pro Pro Ser Gly Ile His Arg Ile Val Leu Val Leu Phe Arg Gln Leu
        115                 120                 125

Gly Arg Gln Thr Val Tyr Ala Pro Gly Trp Arg Gln Gln Phe Asn Thr
    130                 135                 140

Arg Glu Phe Ala Glu Ile Tyr Asn Leu Gly Leu Pro Val Ala Ala Ser
145                 150                 155                 160

Tyr Phe Asn Cys Gln Arg Glu Asn Gly Cys Gly Gly Arg Arg Thr
                165                 170                 175

<210> SEQ ID NO 5
<211> LENGTH: 177
<212> TYPE: PRT
<213> ORGANISM: Arabidopsis thaliana

<400> SEQUENCE: 5

Met Glu Asn Met Gly Thr Arg Val Ile Glu Pro Leu Ile Met Gly Arg
1               5                   10                  15

Val Val Gly Asp Val Leu Asp Phe Phe Thr Pro Thr Thr Lys Met Asn
                20                  25                  30

Val Ser Tyr Asn Lys Lys Gln Val Ser Asn Gly His Glu Leu Phe Pro
            35                  40                  45

Ser Ser Val Ser Ser Lys Pro Arg Val Glu Ile Gly Gly Asp Leu
        50                  55                  60

Arg Ser Phe Phe Thr Leu Val Met Ile Asp Pro Asp Val Pro Gly Pro
65                  70                  75                  80

Ser Asp Pro Phe Leu Lys Glu His Leu His Trp Ile Val Thr Asn Ile
                85                  90                  95

Pro Gly Thr Thr Asp Ala Thr Phe Gly Lys Glu Val Val Ser Tyr Glu
            100                 105                 110

```
Leu Pro Arg Pro Ser Ile Gly Ile His Arg Phe Val Phe Val Leu Phe
            115                 120                 125

Arg Gln Lys Gln Arg Arg Val Ile Phe Pro Asn Ile Pro Ser Arg Asp
130                 135                 140

His Phe Asn Thr Arg Lys Phe Ala Val Glu Tyr Asp Leu Gly Leu Pro
145                 150                 155                 160

Val Ala Ala Val Phe Phe Asn Ala Gln Arg Glu Thr Ala Ala Arg Lys
                165                 170                 175

Arg
```

```
<210> SEQ ID NO 6
<211> LENGTH: 174
<212> TYPE: PRT
<213> ORGANISM: Populus trichocarpa

<400> SEQUENCE: 6
```

```
Met Ala Lys Met Ser Glu Pro Leu Val Val Gly Arg Val Ile Gly Asp
1               5                   10                  15

Val Ile Asp His Phe Thr Ala Asn Val Lys Met Thr Val Thr Tyr Gln
                20                  25                  30

Ser Ser Arg Lys Gln Val Phe Asn Gly His Glu Leu Phe Pro Ser Ala
            35                  40                  45

Val Thr Gln Lys Pro Lys Val Glu Val His Gly Gly Asp Met Arg Ser
    50                  55                  60

Phe Phe Thr Leu Val Met Thr Asp Pro Asp Val Pro Gly Pro Ser Asp
65                  70                  75                  80

Pro Tyr Leu Arg Glu His Leu His Trp Ile Val Thr Asp Ile Pro Gly
                85                  90                  95

Thr Thr Asp Ala Thr Phe Gly Arg Glu Val Val Ser Tyr Glu Met Pro
                100                 105                 110

Arg Pro Asn Ile Gly Ile His Arg Phe Val Phe Leu Leu Phe Lys Gln
            115                 120                 125

Lys Gly Arg Gln Thr Val Thr Thr Pro Ala Ser Arg Asp Lys Phe Asn
130                 135                 140

Thr Arg Lys Phe Ala Glu Glu Asn Glu Leu Asp Leu Pro Val Ala Ala
145                 150                 155                 160

Val Phe Phe Asn Ala Gln Arg Glu Thr Ala Ala Arg Lys Arg
                165                 170
```

```
<210> SEQ ID NO 7
<211> LENGTH: 26
<212> TYPE: DNA
<213> ORGANISM: Artificial sequence
<220> FEATURE:
<223> OTHER INFORMATION: Primer PFT L-1 forward

<400> SEQUENCE: 7
atgtcaaggg acagagatcc tctgag                                          26

<210> SEQ ID NO 8
<211> LENGTH: 23
<212> TYPE: DNA
<213> ORGANISM: Artificial sequence
<220> FEATURE:
<223> OTHER INFORMATION: Primer PFT L-1 reverse

<400> SEQUENCE: 8
ttatgcggtc ctaccaccag agc                                             23
```

```
<210> SEQ ID NO 9
<211> LENGTH: 21
<212> TYPE: DNA
<213> ORGANISM: Artificial sequence
<220> FEATURE:
<223> OTHER INFORMATION: Primer used to detect PFT L-1

<400> SEQUENCE: 9
gagaacttca acaccagaga c                                           21

<210> SEQ ID NO 10
<211> LENGTH: 18
<212> TYPE: DNA
<213> ORGANISM: Artificial sequence
<220> FEATURE:
<223> OTHER INFORMATION: Primer used to detect PFT L-1

<400> SEQUENCE: 10
tccatccacc agagccag                                               18

<210> SEQ ID NO 11
<211> LENGTH: 20
<212> TYPE: DNA
<213> ORGANISM: Artificial sequence
<220> FEATURE:
<223> OTHER INFORMATION: Primer FOR

<400> SEQUENCE: 11
aggttgccaa ccagcctagg                                             20

<210> SEQ ID NO 12
<211> LENGTH: 24
<212> TYPE: DNA
<213> ORGANISM: Artificial sequence
<220> FEATURE:
<223> OTHER INFORMATION: Primer REV

<400> SEQUENCE: 12
aaggtaaaca aacctgtgga tccc                                        24
```

MODULATION OF FLOWERING TIME AND GROWTH CESSATION IN HARDWOOD TREES

CROSS REFERENCE TO RELATED APPLICATIONS

This is the U.S. National Stage of International Application No. PCT/IB2005/003106, filed Sep. 20, 2005, which was published in English as WO 2006/033014 under PCT Article 21(2), which in turn claims priority to GB0420874.0, filed Sep. 20, 2004. Both applications are incorporated herein in their entirety.

This invention relates to the modulation of flowering and growth in trees.

Traditional breeding has had an enormous impact on agriculture. Over 10000 years ago, the first farmers started to select and cross the wild relatives of our cereals in a process that has continued over hundreds of generations. This has lead to incredible gains in yield and quality. Today, crop plants such as wheat, corn, rye and barley, produce over ten times more seed, are more resistant to cold and pathogens and have a dramatically improved quality compared to their wild relatives.

Compared to cereals, breeding in forestry is still in its infancy. The most advanced breeding program for trees has only advanced 3-4 generations and has gained an increase of about 30-40% in productivity. The majority of forests are still either completely unselected or show very low increases in productivity, compared to the wild relatives.

One reason for this is that, in traditional breeding programs, elite individuals for crossing need to be picked from mature trees, which are 20-80 years old. This makes such programs extremely slow.

Modern techniques of "marker assisted breeding" allow important traits to be identified in the DNA of young seedlings, avoiding the need to wait until the tree is mature. However, trees are extremely late flowering plants and many trees do not flower for the first time until they are 15-20 years old. Since plants can only be used for crosses in breeding programs when they have flowered, tree plant breeding remains slow, even though important traits can be identified at the seedling stage.

The ability to induce early flowering would be extremely useful in tree breeding programs.

The LEAFY gene is known to control flowering in *Arabidopsis thaliana* (Weigel, D. & Nilsson, O. (1995) Nature 377, 495-500). LEAFY has also been shown to induce early flowering in unrelated species, including hybrid aspen trees, which are one of the latest flowering species known. However, the effect of LEAFY is very variable and some species (such as conifer trees) do not respond at all to LEAFY expression. Furthermore, not all poplar species and clones respond in the same way (Rottmann W H et al 2000. Plant J. 22:235-245) and it remains to be seem whether the 35S::LEAFY aspen flowers are fertile. In many species, the flowering induced by LEAFY over-expression is abnormal and non-physiological (Nilsson, O. & Weigel, D. (1997) *Curr. Opin. Biotechnol.* 8 195-199, Peña L, Martin-Trillo M, et al *Nat Biotechnol* (2001) 19:263-267).

Other genes specifically associated with the timing of flowering have been extensively studied in *Arabidopsis*, and several of them, including CO, FCA, AP1, GI and SOC1, have been shown to cause early flowering in *Arabidopsis* when over expressed (Simpson G G et al (1999) Annu Rev Cell Dev Biol. 15 519-50). However, except for AP1, which can cause early flowering in citrus trees (Peña et al., 2001), these flowering-time genes do not produce early flowering in other non-*Arabidopsis* species.

Transgenic *Arabidopsis* plants can also be induced to flower much earlier in their annual life cycle by fusing the *Arabidopsis* gene FT to the strong and constitutive Cauliflower Mosaic Virus 35S promoter (35S promoter) (WO99/53070). FT belongs to a set of *Arabidopsis* flowering time genes that are grouped in the so called "long day pathway", meaning that they cause *Arabidopsis* to flower much earlier under long day conditions than short day conditions. It has not been shown that perennial plants display this response and the role of FT-like genes in perennial plants is not clear.

The present inventors have successfully identified and cloned the FT-like genes PFT1 and PFT2 in poplars (also called PFT-L1 and PFT-L2). PFT1 has been shown to have a dramatic effect on the timing of flowering in perennial plant species. This has important applications for forestry, for example in tree breeding programs.

One aspect of the invention provides a method of inducing early flowering in a perennial plant comprising;
expressing a heterologous nucleic acid encoding a PFT polypeptide within cells of said perennial plant.

Expression of the PFT polypeptide within cells of the perennial plant induces early flowering in the perennial plant.

Early flowering is induced during the vegetative growth phase of a perennial plant and may be one or more years, for example, 5, 15 or 20 or more years, before flowering would normally occur in the plant.

The present inventors have also shown that the PFT gene affects plant growth and, in particular, it represses the growth cessation or dormancy which is induced by short day length, for example in the autumn. This unexpected effect potentially allows the extension of the growing season of perennial plants. This may also have important commercial applications, for example in forestry.

Another aspect of the invention provides a method of repressing short day induced growth cessation in a perennial plant comprising;
expressing a heterologous nucleic acid encoding a PFT polypeptide within cells of said perennial plant.

Short-day induced growth cessation is the period of dormancy which occurs in perennial plants in response to short day length, for example in autumn and winter.

Expression of the PFT polypeptide within cells of the perennial plant represses short day induced growth cessation in the plant and may be useful, for example in extending the plant growing season.

In some embodiments, a perennial plant which expresses a heterologous nucleic acid encoding a PFT polypeptide may be grafted to another plant to induce early flowering or repress short day induced growth cessation in the other plant. A method of inducing early flowering or repressing short day induced growth cessation in a first perennial plant may comprise;
expressing a heterologous nucleic acid encoding a PFT polypeptide within cells of a second perennial plant, and;
grafting all or part of said second perennial plant onto said first perennial plant,
wherein said graft induces early flowering and/or represses short day induced growth cessation in the first perennial plant Methods and means of grafting perennial plants are well known in the art. A suitable graft may comprise one or more cells of the second perennial plant. Typically, a stem or shoot of the second plant perennial comprising the cambium layer will be employed.

A perennial plant is a plant which has a life cycle which takes longer than 2 years and involves a long juvenile period in which only vegetative growth occurs. This is contrasted with an annual plant such as *Arabidopsis thaliana*, which has a life cycle which is completed in one year.

A perennial plant may be a gymnosperm (non-flowering plant) or an angiosperm (flowering plant). Angiosperms are divided into two broad classes and a perennial plant may be a monocotyledonous or dicotyledonous angiosperm.

The term 'flowering' as used herein encompasses the production of flowers in flowering species and reproductive structures in non-flowering species.

In preferred embodiments, a perennial plant is a woody plant which has hard lignified tissues and forms a bush or tree. Preferred perennial plants are trees (i.e. plants of tree forming species).

Examples of woody perennial plants include conifers such as cypress, Douglas fir, fir, sequoia, hemlock, cedar, juniper, larch, pine, redwood, spruce and yew; hardwoods such as acacia, eucalyptus, hornbeam, beech, mahogany, walnut, oak, ash, willow, hickory, birch, chestnut, poplar, alder, maple and sycamore; fruit bearing plants such as apple, plum, pear, banana, orange, kiwi, lemon, cherry, grapevine and fig; and other commercially significant plants, such as cotton, bamboo and rubber.

In some preferred embodiments, a PFT polypeptide may have the amino acid sequence of SEQ ID NO: 1 or may be a fragment or variant of the SEQ ID NO: 1 sequence which retains PFT activity, including for example induction of early flowering or repression of short-day induced growth cessation.

A PFT polypeptide which is a variant of SEQ ID NO: 1 may comprise an amino acid sequence which shares greater than 60% sequence identity with the amino acid sequence of SEQ ID NO: 1, preferably greater than 65%, greater than 70%, greater than 80%, greater than 90% or greater than 95%.

In other embodiments, a PFT polypeptide which is a variant of SEQ ID NO: 1 may share greater than 60% sequence similarity with the amino acid sequence of SEQ ID NO: 1, preferably greater than 65%, greater than 70%, greater than 80%, greater than 90% or greater than 95%.

Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Particular amino acid sequence variants may differ from a known PFT polypeptide sequence as described herein by insertion, addition, substitution or deletion of 1 amino acid, 2, 3, 4, 5-10, 10-20 20-30, 30-50, or more than 50 amino acids.

Sequence similarity and identity are commonly defined with reference to the algorithm GAP (Wisconsin Package, Accelerys, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4.

Use of GAP may be preferred but other algorithms may be used, e.g. BLAST (which uses the method of Altschul et al. (1990) *J. Mol. Biol.* 215: 405-410), *FASTA* (which uses the method of Pearson and Lipman (1988) *PNAS USA* 85: 2444-2448), or the Smith-Waterman algorithm (Smith and Waterman (1981) *J. Mol. Biol.* 147: 195-197), or the TBLASTN program, of Altschul et al. (1990) supra, generally employing default parameters. In particular, the psi-Blast algorithm (Nucl. Acids Res. (1997) 25 3389-3402) may be used.

Sequence comparison may be made over the full-length of the relevant sequence described herein, or may be over a contiguous sequence (i.e. a 'window') of at least 50, 75, 100, 150 or more amino acids or nucleotide triplets, compared with the relevant amino acid sequence or nucleotide sequence.

A PFT polypeptide is preferably active in inducing early flowering in a perennial plant and/or repressing short-day induced growth cessation.

A PFT polypeptide may also be characterised by its phylogenetic relationship to other flowering genes. A phylogenetic analysis of these genes is shown in FIG. 5. A PFT polypeptide as described herein is preferably a member of the FT clade of flower activators, which is the phylogenetic sub-tree which encompasses as nodes the sequences of *Arabidopsis* FT and TFT, Citrus CiFT and *Populus* PFT1 and PFT2, but not the sequences of *Arabidopsis* TFL1 or *Populus* PBFT, as defined by PAUP*v4.0 (Swofford D. (2003) PAUP*. Phylogenetic Analysis Using Parsimony (*and Other Methods). Version 4. Sinauer Associates, Sunderland, Mass.).

A PFT polypeptide suitable for use in the present methods may be any plant PFT polypeptide, preferably a perennial plant PFT polypeptide, for example a woody perennial plant PFT polypeptide, such as a poplar PFT polypeptide.

In some embodiments, a PFT polypeptide may not be a PFT polypeptide from an annual plant, for example from a *Brassicae* spp such as *Arabidopisis thaliana*. The *Arabidopsis* FT polypeptide sequence is encoded by the gene locus AT1G65480 and has the database accession numbers NP_176726.1, AAM91747.1 and AAL38819.1 (see also SEQ ID NO: 3).

Nucleic acids as described herein may be wholly or partially synthetic. In particular, they may be recombinant in that nucleic acid sequences which are not found together in nature (do not run contiguously) have been ligated or otherwise combined artificially. Alternatively they may have been synthesised directly e.g. using an automated synthesiser.

A nucleic acid encoding a PFT polypeptide may comprise or consist of the nucleotide sequence of SEQ ID NO: 2 or may be a variant or fragment of the SEQ ID NO: 2 sequence.

A variant sequence may be a mutant, homologue, or allele of the SEQ ID NO: 2 sequence and may differ from the sequence of SEQ ID NO: 2 by one or more of addition, insertion, deletion or substitution of one or more nucleotides in the nucleic acid, leading to the addition, insertion, deletion or substitution of one or more amino acids in the encoded polypeptide. Of course, changes to the nucleic acid that make no difference to the encoded amino acid sequence are included.

A nucleic acid encoding a PFT polypeptide, which has a nucleotide sequence which is a variant of the SEQ ID NO: 2 sequence may comprise a sequence having at least 60% sequence identity with the nucleic acid sequence of SEQ ID NO:2, than 65%, greater than 70%, greater than 80%, greater than 90% or greater than 95%. Sequence identity is described above.

A fragment or variant may comprise a sequence which encodes a functional PFT polypeptide i.e. a polypeptide which retains one or more functional characteristics of the polypeptide encoded by the wild-type PFT gene, for example, the ability to stimulate early flowering in a perennial plant and/or repress short-day induced growth cessation.

In other embodiments, a nucleic acid encoding a PFT polypeptide, which has a nucleotide sequence which is a variant of the SEQ ID NO: 2 sequence may selectively hybridise under stringent conditions with the nucleic acid sequence of SEQ ID NO: 2 or the complement thereof.

Stringent conditions include, e.g. for hybridization of sequences that are about 80-90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS.

An alternative, which may be particularly appropriate with plant nucleic acid preparations, is a solution of 5×SSPE (final 0.9 M NaCl, 0.05M sodium phosphate, 0.005M EDTA pH 7.7), 5×Denhardt's solution, 0.5% SDS, at 50° C. or 65° C. overnight. Washes may be performed in 0.2×SSC/0.1% SDS at 65° C. or at 50-60° C. in 1×SSC/0.1% SDS, as required.

Hybridisation methods may also be used to determine the presence of one of the nucleotide sequences of the present invention within the genetic context of an individual plant, for example a transgenic plant, which may be produced as described in more detail below. This may be useful in plant breeding programmes e.g. to directly select plants containing alleles which are responsible for desirable traits in that plant species, either in parent plants or in progeny (e.g. hybrids, F1, F2 etc.).

In some embodiments, a PFT nucleic acid may not be a PFT nucleic acid from an annual plant, for example from a *Brassicae* spp such as *Arabidopisis thaliana*. The *Arabidopsis* FT nucleic acid sequence is encoded by the gene locus AT1G65480 and has the database accession numbers NM_105222.2, AY133813.1, and AY065378.1.

Nucleic acid may of course be double- or single-stranded, cDNA or genomic DNA, or RNA. The nucleic acid may be wholly or partially synthetic, depending on design. Naturally, the skilled person will understand that where the nucleic acid includes RNA, reference to the sequence shown should be construed as reference to the RNA equivalent, with U substituted for T.

A regulatory sequence operably linked to a PFT nucleic acid sequence is preferably heterologous or foreign to the PFT nucleic acid sequence (e.g. from a different species, class or type of organism). Preferably, the regulatory sequence is a plant specific regulatory sequence to provide for efficient expression within a plant cell.

"Heterologous" indicates that the gene/sequence of nucleotides in question or a sequence regulating the gene/sequence in question, has been introduced into said cells of the plant or an ancestor thereof, using genetic engineering or recombinant means, i.e. by human intervention. Nucleotide sequences which are heterologous to a plant cell may be non-naturally occurring in cells of that type, variety or species (i.e. exogenous or foreign) or may be sequences which are non-naturally occurring in that sub-cellular or genomic environment of the cells or may be sequences which are non-naturally regulated in the cells i.e. operably linked to a non-natural regulatory element. In some cases, the sequence of a heterologous nucleic acid may be identical to an endogenous nucleic acid sequence which exists naturally in the plant.

A plant specific regulatory sequence or element preferentially directs the expression (i.e. transcription) of a nucleic acid within a plant cell relative to other cell types. For example, expression from such a sequence may be reduced or abolished in non-plant cells, such as bacterial or mammalian cells.

Many suitable regulatory sequences are known in the art and may be used in accordance with the invention. Examples of suitable regulatory sequences may be derived from a plant virus, for example the Cauliflower Mosaic Virus 35S (CaMV 35S) gene promoter that is expressed at a high level in virtually all plant tissues (Benfey et al, (1990) EMBO J 9: 1677-1684). Leaf specific promoters may also be used (see for example Lagrange et al Plant Cell. 1997 9 (8): 1469-1479). Other suitable constitutive regulatory elements include the cauliflower mosaic virus 19S promoter; the Figwort mosaic virus promoter; and the nopaline synthase (nos) gene promoter (Singer et al., Plant Mol. Biol. 14:433 (1990); An, Plant Physiol. 81:86 (1986)).

In some embodiments, a regulatory sequence operatively linked to the nucleic acid sequence may be inducible, as described below.

In some embodiments, the promoter may be a promoter which ha increased activity relative to the native PFT promoter in short day conditions i.e. when day length is reduced, for example in autumn, the promoter retains all or some activity relative to the native PFT promoter.

The heterologous nucleic acid may be contained on a nucleic acid construct or vector. The construct or vector is preferably suitable for transformation into and/or expression within a plant cell.

A construct or vector comprising nucleic acid as described above need not include a promoter or other regulatory sequence, particularly if the vector is to be used to introduce the nucleic acid into cells for recombination into the genome.

Constructs and vectors may further comprise selectable genetic markers consisting of genes that confer selectable phenotypes such as resistance to antibiotics such as kanamycin, hygromycin, phosphinotricin, chlorsulfuron, methotrexate, gentamycin, spectinomycin, imidazolinones, glyphosate and d-amino acids.

Those skilled in the art can construct vectors and design protocols for recombinant gene expression, for example in a microbial or plant cell. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 3rd edition, Sambrook et al, 2001, Cold Spring Harbor Laboratory Press and *Protocols in Molecular Biology*, Second Edition, Ausubel et al. eds. John Wiley & Sons, 1992. Specific procedures and vectors previously used with wide success upon plants are described by Bevan, Nucl. Acids Res. (1984) 12, 8711-8721), and Guerineau and Mullineaux, (1993) Plant transformation and expression vectors. In: Plant Molecular Biology Labfax (Croy RRD ed) Oxford, BIOS Scientific Publishers, pp 121-148.

In some preferred embodiments, vectors may include a kanamycin resistance gene as a selectable marker. This may be included in a cassette containing the nos (nopaline synthase) promoter and the nos terminator. For *agrobacterium* transformation, this is conveniently positioned near the border of a T-DNA construct (Hellens, R. P. et al., Plant Molecular Biology 42:819-832, 2000). The PFT coding sequence in such a vector may be operably linked to a constitutive promoter such as the 35S CMV promoter (De-Loose, M. et al. Euphytica 85: 209-216, 1995) or an inducible promoter such as the HSP promoter (Severin K. and Schöffl F. 1990. *Plant Mol. Biol.* 15: 827-833). 3' of the coding sequence is preferably a termination signal, such as the T35S termination signal.

Some preferred vectors may be based on the pPZP200 binary vector which comprises the following elements; borders of the pTiT37 T-DNA, bom site of pBR322 (mobilization from *E. coli* to *Agrobacterium*), col E1 origin of replication in *E. coli*, pVS1 origin of replication in *Agrobacterium*, spectinomycin bacterial marker and the pUC18 multiple cloning site (MCS) (Hajdukiewicz et al. Plant Molecular Biology 25, 989-994, 1994).

Examples of preferred vectors include vectors based on Gateway™ vectors (Invitrogen) such as pK2GW7 (Karimi M. et al (2002) Trends in Plant Science 7 (5): 193-189).

In some embodiments, the vector does not contain PFT coding sequence operably linked to both the 35S CMV 200 bp promoter and the nopaline synthetase transcriptional terminator (nos), as described in Walden et al (1994) Plant Mol. Biol. 26 1521-1528 and/or the pSKI backbone sequence. For example, in some embodiments, the vectors pSKI059, pSKI089 or pSKI060 as described in WO99/53070 may be excluded.

Early flowering in transgenic plants is often phenotypically abnormal because the induced flowers must compete for nutrients with growing shoots and leaves. The use of inducible promoters to drive PFT expression in perennial plants may be useful in producing phenotypically normal flowering.

A method of inducing early flowering in a perennial plant may comprise;

providing a perennial plant comprising an nucleic acid encoding a PFT polypeptide, said nucleic acid being operably linked to an inducible promoter, activating said inducible promoter to express said nucleic acid such that production of flower buds is stimulated in said plant, deactivating said inducible promoter to stop expression of said nucleic acid, causing or allowing the plant to deactivate growth and become dormant, and;

causing or allowing the plant to reactivate growth, such that early flowering is induced from said flower buds.

Growth of a plant may be deactivated by exposing the plant to conditions which induce dormancy. Conditions which induce dormancy include short day length and decreased temperature.

Growth may be reactivated in a dormant plant by exposing the plant to conditions which induce growth. Conditions which induce growth include increased temperature and, optionally, increased day length.

Inducible promoters are well known in the art and include, for example the HSP promoter (Severin K. and Schoffl F. 1990. *Plant Mol. Biol.* 15: 827-833). In essence, expression under the control of an inducible promoter is "switched on" or increased in response to an applied stimulus (which may be generated within a cell or provided exogenously). The nature of the stimulus varies between promoters. Whatever the level of expression is in the absence of the stimulus, expression from any inducible promoter is increased in the presence of the correct stimulus. The preferable situation is where the level of expression increases in the presence of the relevant stimulus by an amount effective to alter a phenotypic characteristic i.e. to stimulate flowering or repress growth cessation. Thus, an inducible (or "switchable") promoter may be used which causes a basic level of expression in the absence of the stimulus which level is too low to bring about the desired phenotype (and may in fact be zero). Upon application of the stimulus, expression is increased (or switched on) to a level that causes alterations in the plant phenotype.

Many other examples of inducible promoters will be known to those skilled in the art and include, for example steroid inducible promoters (Schena et al PNAS USA (1991) 88 (23): 10421-10425), ethanol inducible promoters (Salter et al (1998) The Plant Journal 16 1 127), copper-inducible promoters (Mett et al., Proc. Natl. Acad. Sci. USA 90:4567-4571 (1993); Furst et al., Cell 55:705-717 (1988)); tetracycline and chlor-tetracycline-inducible promoters (Gatz et al., Plant J. 2:397-404 (1992); Roder et al., Mol. Gen. Genet. 243:32-38 (1994); Gatz, Meth. Cell Biol. 50:411-424 (1995)); ecdysone inducible promoters (Christopherson et al., Proc. Natl. Acad. Sci. USA 89:6314-6318 (1992) heat shock inducible promoters (Takahashi et al., Plant Physiol. 99:383-390 (1992)) lac operon promoters, which are used in combination with a constitutively expressed lac repressor to confer, for example, IPTG-inducible expression (Wilde et al., EMBO J. 11:1251-1259 (1992)), nitrate-inducible promoters, for example derived from the spinach nitrite reductase gene (Back et al., Plant Mol. Biol. 17:9 (1991)), light-inducible promoters, such as that associated with the small subunit of RuBP carboxylase or the LHCP gene families (Feinbaum et al., Mol. Gen. Genet. 226:449 (1991)), salicylic acid inducible promoters (Uknes et al., Plant Cell 5:159-169 (1993)); and plant hormone-inducible promoters (Yamaguchi-Shinozaki et al., Plant Mol. Biol. 15:905 (1990)).

The perennial plant may be allowed to become dormant by exposing the plant to short days and decreased temperatures. Outside plants are typically exposed to short days in autumn and winter and remain in a dormant state until day length and temperature increases in the spring. In other embodiments, plants may be exposed to short days artificially by manipulating the conditions in a greenhouse as described herein.

The perennial plant may then be allowed to grow after the dormancy period by exposing the plant to long days and increased temperatures. Outside plants are typically exposed to long days and increased temperatures in spring and summer and remain in an active growth state until day length decreases in the autumn. In other embodiments, plants may be exposed to long days and increased temperatures to induce active growth artificially by manipulating the conditions in a greenhouse as described herein.

Another aspect of the invention provides a method of producing a perennial plant comprising incorporating a heterologous nucleic acid encoding a PFT polypeptide, or a vector comprising such a nucleic acid, into a perennial plant cell by means of transformation and;

regenerating a perennial plant from one or more transformed cells.

A perennial plant produced by such a method may flower earlier than control plants and/or may show partial or complete repression of short day induced growth cessation.

Preferably, the nucleic acid recombines with the cell genome nucleic acid such that it is stably incorporated therein.

The PFT polypeptide, the encoding nucleic acid, and/or the vector comprising the nucleic acid are described in more detail above and may be heterologous (e.g. exogenous or foreign) to the cell transformed therewith.

When introducing a chosen gene construct into a cell, certain considerations must be taken into account, well known to those skilled in the art. The nucleic acid to be inserted should be assembled within a construct that contains effective regulatory elements that will drive transcription. There must be available a method of transporting the construct into the cell. Once the construct is within the cell membrane, integration into the endogenous chromosomal material either will or will not occur. Finally, the target cell type is preferably such that cells can be regenerated into whole plants.

Techniques well known to those skilled in the art may be used to introduce nucleic acid constructs and vectors into woody plant cells to produce transgenic plants with the properties described herein. *Agrobacterium* transformation is one method widely used by those skilled in the art to transform woody plant species, in particular hardwood species such as poplar. Production of stable, fertile transgenic plants is now routine in the art:(Toriyama, et al. (1988) *Bio/Technology* 6, 1072-1074; Zhang, et al. (1988) *Plant Cell Rep.* 7, 379-384; Zhang, et al. (1988) *Theor Appl Genet* 76, 835-840; Shimamoto, et al. (1989) Nature 338, 274-276; Datta, et al. (1990) *Bio/Technology* 8, 736-740; Christou, et al. (1991) *Bio/Technology* 9, 957-962; Peng, et al. (1991) International Rice Research Institute, Manila, Philippines 563-574; Cao, et al. (1992) *Plant Cell Rep.* 11, 585-591; L1, et al. (1993) *Plant Cell Rep.* 12, 250-255; Rathore, et al. (1993) *Plant Molecular Biology* 21, 871-884; Fromm, et al. (1990) *Bio/Technology* 8, 833-839; Gordon-Kamm, et al. (1990) *Plant Cell* 2, 603-618; D'Halluin, et al. (1992) *Plant Cell* 4, 1495-1505; Walters, et al. (1992) *Plant Molecular Biology* 18, 189-200; Koziel, et al. (1993) *Biotechnology* 11, 194-200; Vasil, I. K. (1994) *Plant Molecular Biology* 25, 925-937; Weeks, et al. (1993) *Plant Physiology* 102, 1077-1084; Somers, et al. (1992) *Bio/Technology* 10, 1589-1594; WO92/14828; Nilsson, O. et al (1992) *Transgenic Research* 1, 209-220).

Other methods, such as microprojectile or particle bombardment (U.S. Pat. No. 5,100,792, EP-A-444882, EP-A-434616), electroporation (EP 290395, WO 8706614), microinjection (WO 92/09696, WO 94/00583, EP 331083, EP 175966, Green et al. (1987) *Plant Tissue and Cell Culture*, Academic Press), direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d)) may be preferred where *Agrobacterium* transformation is inefficient or ineffective, for example in some gymnosperm species.

Physical methods for the transformation of plant cells are reviewed in Oard, 1991, *Biotech. Adv.* 9: 1-11.

Alternatively, a combination of different techniques may be employed to enhance the efficiency of the transformation process, e.g. bombardment with *Agrobacterium* coated microparticles (EP-A-486234) or microprojectile bombardment to induce wounding followed by co-cultivation with *Agrobacterium* (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol I, II and III, Laboratory Procedures and Their Applications*, Academic Press, 1984, and Weissbach and Weissbach, Methods for Plant Molecular Biology, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

A perennial plant regenerated from said plant cell be sexually or asexually propagated or grown to produce off-spring or descendants.

Another aspect of the invention provides a perennial plant which is produced by a method described herein, wherein said plant shows early flowering and/or repressed short-day induced growth cessation relative to control plants.

Also provided is any part or propagule of such a plant, for example seeds, selfed or hybrid progeny and descendants.

Such a perennial plant may comprise a heterologous nucleic acid encoding PFT polypeptide, as described herein.

The present inventors have shown that early flowering may be induced in both male and female perennial plants of dioecious species. Furthermore, in contrast to the effect of LEAFY over-expression, the induced flowers have a normal phenotype and the male flowers produce pollen. Methods of the invention are therefore particularly useful in the selective breeding of perennial plants.

A method of producing a perennial plant having a desired trait may comprise;
producing a male of a dioecious perennial plant species having a desired trait and expressing a heterologous nucleic acid encoding a PFT polypeptide within its cells, thereby inducing early flowering
allowing said male perennial plant to flower and;
crossing said male with a female plant to produce progeny plants having the desired trait.

A method may comprise selecting early flowering plants having the desired trait from said progeny. Selected progeny having the desired trait may then be subjected to further crossing.

In some embodiments, the female plant which is crossed with the male plant may also express a heterologous nucleic acid encoding a PFT polypeptide within its cells.

A method of producing a perennial plant having a desired trait may comprise;
producing a female of the dioecious perennial plant species having a desired trait and expressing a heterologous nucleic acid encoding a PFT polypeptide within its cells, thereby inducing early flowering,
allowing said female perennial plant to flower and;
crossing said female tree plant with a male plant to produce progeny plants having the desired trait.

A method may comprise selecting early flowering plants having the desired trait from said progeny. Selected progeny having the desired trait may then be subjected to further crossing.

In some embodiments, the male plant which is crossed with the female may also express a heterologous nucleic acid encoding a PFT polypeptide within its cells.

Methods of the invention may also be useful in the selective breeding of monocieous perennial plants A method of producing a perennial plant having a desired trait may comprise;
providing or producing a monocieous perennial plant having a desired trait and comprising a heterologous nucleic acid encoding a PFT polypeptide within its cells,
expressing said nucleic acid to induce flowering of said plant and;
producing progeny from said plant which have the desired trait.

Progeny may be produced by self-crossing the plant or by crossing the plant with a wild-type plant or a plant comprising said heterologous nucleic acid.

In-bred plant lines are useful in plant breeding. Methods of the invention may also be useful in the production of in-bred lines in perennial plants, in particular woody perennial plants, such as tree-forming species.

To produce an inbred line, a monocieous or dioceous plant having a desired trait and produced as described above may be repeatedly crossed with itself or an identical plant. Healthy progeny from each self-crossing may be selected for the next self-crossing to avoid fixation of deleterious alleles.

A plant line is inbred when its characteristics remain constant after several rounds of self-crossing.

Inbred lines are especially useful in the production of hybrids. Hybrids from inbred lines are generally uniform and robust, in contrast to hybrids from other cultivars, which have variable characteristics. Furthermore, hybrids from inbred lines may show increased productivity and resistance to environmental stress ('hybrid vigor'). Inbred lines produced as described above may be crossed to produce hybrids having properties from both parent lines.

PFT polypeptides and encoding nucleic acid are described in more detail above.

A desired trait may include growth rate, size, form, timing of growth, seed germination, wood properties, leaf characteristics, cone morphology, pest resistance, and capacity to withstand climatic stresses. For commercial forestry production, growth rate, disease resistance, fiber strength, fiber length, wood chemistry and other wood properties are particularly important.

Methods and means of carrying out selective breeding programs are well known in the art.

Other aspects of the invention relate to the PFT1 polypeptide and encoding nucleic acid, which were identified and characterised by the present inventors.

An aspect of the invention provides an isolated nucleic acid comprising or consisting of a nucleotide sequence which encodes an amino acid sequence that has at least 80% amino acid sequence identity with the amino acid sequence shown in SEQ ID NO: 1.

For example, the nucleotide sequence may encode an amino acid sequence that has at least 85%, 90%, 95% or 98% amino acid sequence identity with the amino acid sequence shown in SEQ ID NO: 1. In some embodiments, the nucleic acid may encode the amino acid sequence shown in SEQ ID NO: 1.

An isolated nucleic acid comprising a nucleotide sequence having at least 80%, 85%, 90%, 95% or 98% sequence identity with the nucleic acid sequence shown in SEQ ID NO: 1. In some embodiments, the nucleic acid may have the nucleic acid sequence shown in SEQ ID NO: 1.

Expression of the isolated nucleic acid in a plant may result in the induction of flowering and/or the repression of short day induced growth cessation.

A nucleic acid as described above may be comprised in a nucleic acid vector suitable for transformation of a plant cell.

Nucleic acid and vectors as described herein may be contained in a host cell, for example a plant cell, in particular a plant cell from a woody species, such as poplar. A host cell may be produced by incorporating the nucleic acid or vector into the cell by means of transformation, using methods well known in the art and described in more detail above. The nucleic acid or vector may recombine with the cell genome nucleic acid such that it is stably incorporated therein.

A plant host cell may be suitable for regenerating a plant, in particular a woody plant. A plant regenerated from the plant cell may show early flowering and/or repression of short day induced growth cessation and may be sexually or asexually propagated or grown to produce off-spring or descendants.

Nucleic acid, vectors, host cells and transgenic plants are all described in more detail above.

Other aspects of the invention relate the use of sense and anti-sense PFT nucleic acids to repress PFT expression.

A method of delaying flowering or promoting short day induced growth cessation in a perennial plant may comprise;

expressing in cells of the plant a sense or anti-sense nucleic acid comprising a nucleic acid sequence capable of hybridizing under stringent conditions to a nucleic acid encoding a PFT polypeptide or the complement thereof, said expression reducing the expression of the PFT polypeptide, thereby delaying flowering and/or promoting short day induced growth cessation.

The use of anti-sense and RNAi approaches to down-regulate plant gene expression is well-established in the art.

Anti-sense oligonucleotides may be designed to hybridise to the complementary sequence of nucleic acid, pre-mRNA or mature mRNA, interfering with the production of PFT polypeptide so that its expression is reduced or completely or substantially prevented. In addition to targeting coding sequence, anti-sense techniques may be used to target control sequences of a gene, e.g. in the 5' flanking sequence, whereby the antisense oligonucleotides can interfere with the sequences which control expression. The construction of antisense sequences and their use is described for example in Peyman and Ulman, Chemical Reviews, 90:543-584, (1990) and Crooke, Ann. Rev. Pharmacol. Toxicol., 32:329-376, (1992).

Oligonucleotides may be generated in vitro or ex vivo for administration or anti-sense RNA may be generated in vivo within cells in which down-regulation is desired. Thus, double-stranded DNA may be placed under the control of a promoter in a "reverse orientation" such that transcription of the anti-sense strand of the DNA yields RNA which is complementary to normal mRNA transcribed from the sense strand of the target gene. The complementary anti-sense RNA sequence is thought then to bind with mRNA to form a duplex, inhibiting translation of the endogenous mRNA from the target gene into protein.

The complete sequence corresponding to the coding sequence in reverse orientation need not be used. For example fragments of sufficient length may be used. It is a routine matter for the person skilled in the art to screen fragments of various sizes and from various parts of the coding or flanking sequences of a gene to optimise the level of anti-sense inhibition. It may be advantageous to include the initiating methionine ATG codon, and perhaps one or more nucleotides upstream of the initiating codon. A suitable fragment may have about 14-23 nucleotides, e.g. about 15, 16 or 17.

An alternative to anti-sense is to use a copy of all or part of the target gene inserted in sense, that is the same, orientation as the target gene, to achieve reduction in expression of the target gene by co-suppression; Angell & Baulcombe (1997) The EMBO Journal 16, 12:3675-3684; and Voinnet & Baulcombe (1997) Nature 389: pg 553). Double stranded RNA (dsRNA) has been found to be even more effective in gene silencing than both sense or antisense strands alone (Fire A. et al Nature, 391, (1998)). dsRNA mediated silencing is gene specific and is often termed RNA interference (RNAi).

RNA interference is a two-step process. First, dsRNA is cleaved within the cell to yield short interfering RNAs (siRNAs) of about 21-23 nucleotides length with 5' terminal phosphate and 3' short overhangs (~2 nt). The siRNAs target the corresponding mRNA sequence specifically for destruction (Zamore P. D. Nature Structural Biology, 8, 9, 746-750, (2001)

RNAi may be also be efficiently induced using chemically synthesized siRNA duplexes of the same structure with 3'-overhang ends (Zamore P D et al Cell, 101, 25-33, (2000)). Synthetic siRNA duplexes have been shown to specifically suppress expression of endogenous and heterologous genes in a wide range of mammalian cell lines (Elbashir S M. et al. Nature, 411, 494-498, (2001)).

Materials and Methods for the manipulation and expression of nucleic acid constructs, the transformation of host cells and the regeneration of transgenic plants are described in more detail above.

Control experiments may be performed as appropriate in the methods described herein. The performance of suitable controls is well within the competence and ability of a skilled person in the field.

The disclosures of all documents mentioned herein are incorporated herein by reference.

Various further aspects and embodiments of the present invention will be apparent to those skilled in the art in view of the present disclosure.

Certain aspects and embodiments of the invention will now be illustrated by way of example and with reference to the figure described below.

FIG. 1 shows sequence comparisons of PFT L-1 to related proteins in Populus and Arabidopsis with one-letter amino acid code. The proteins are PFT1 from Populus trichocarpa (SEQ ID NO:1); FT from Arabidopsis thaliana (SEQ ID NO:3); TSF from Arabidopsis thaliana (SEQ. ID NO:4); TFL1 from Arabidopsis thaliana (SEQ ID N); CEN L-1 from Populus trichocarpa (SEC) ID NO:6). Black boxes indicate identical amino acids, shade boxes indicate amino acids with similar properties and dots indicate gaps introduced to optimize alignment.

FIG. 2 shows growth curves for wild type, 35S::PFT L-1 and 35S::PHYA transgenic plants grown in long days (16 h light, 8 h dark 300 µE, 23° C.) for 23 days then transferred to short days (8 h light, 16 h dark 300 µE, 23° C.) for another 63 days with growth measurement twice per week.

SEQ ID NO: 1 is the amino acid sequence of Poplar PFT1.

SEQ ID NO: 2 is the nucleotide coding sequence of Poplar PFT1.

SEQ ID NO: 3 is the amino acid sequence of Arabidopsis FT.

EXPERIMENTAL

Identifying PFT1

Coding sequences which displayed some homology to the Arabidopsis thaliana gene FT were identified through a BLAST against the Populus trichocarpa genome sequence.

Two sequences were identified, called PFT1 and PFT2 (also called PFT-L1 and PFT-L2, for Populus FT-like 1 and 2).

Figure 1:
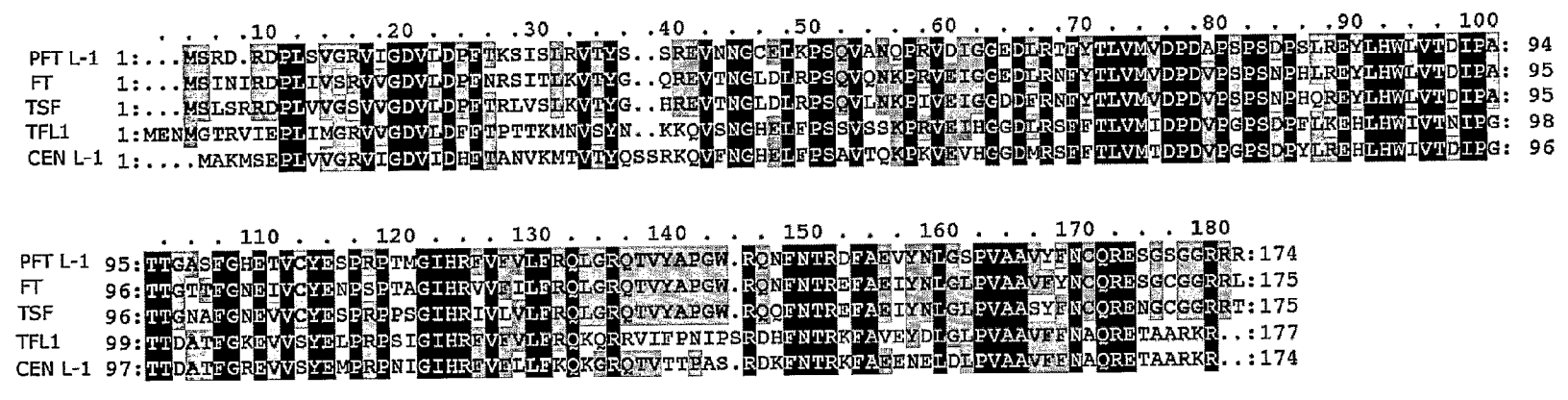

Sequence comparisons showed that these genes were more similar to the Arabidopsis genes FT and TSF, than to the closely related Arabidopsis gene TFL1 (FIG. 1) Protein sequences were aligned using the Clustal W program (Thomson et al; 1994 Nucleic Acids Res 22, 4673-4680) and the results shown in FIG. 1.

Figure 5:
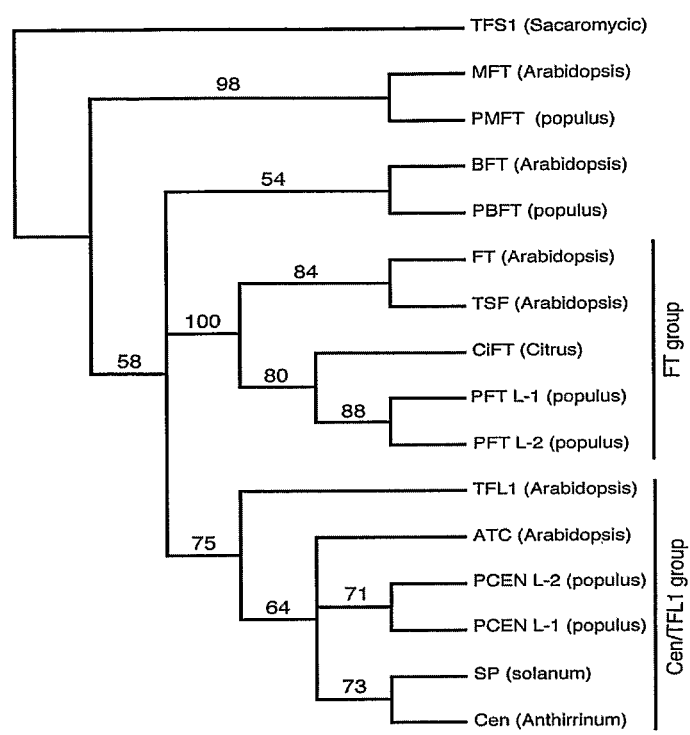
FIG. 5 shows phylogenetical analysis of the PFT sequences.

A phylogenetic tree was performed based on protein sequence encoded by PFT1 related proteins from plants with the yeast protein TSF1 as outgroup. The following PFT1 genes were included: TSF1 from Saccharomyces pombe; MFT from Arabidopsis thaliana; PMFT from Populus tremula; BFT from Arabidopsis thaliana; FT from Arabidopsis thaliana; CiFT from Citrus sinensis; PFT L-1 from Populus trichocarpa; TFL1 from Arabidopsis thaliana; ATC from Arabidopsis thaliana; SP from Solanum lycopersicum; CEN from Anthirrinum majus. PFT L-2 from Populus trichocarpa; PCEN L-1 from Populus trichocarpa; PBFT from Populus trichocarpa. Branch length reflects evolutionary distances. The phylogenetical analysis was made with the PAUP* program (version 4.0b10; Swofford, 2003) and confirmed that PFTL-1 and PFT2 belonged to the FT clade of flower activators rather than to the TFL1/CEN clade of floral repressors (FIG. 5).

Early Flowering Induced by 35S::PFT1

Figure 4:
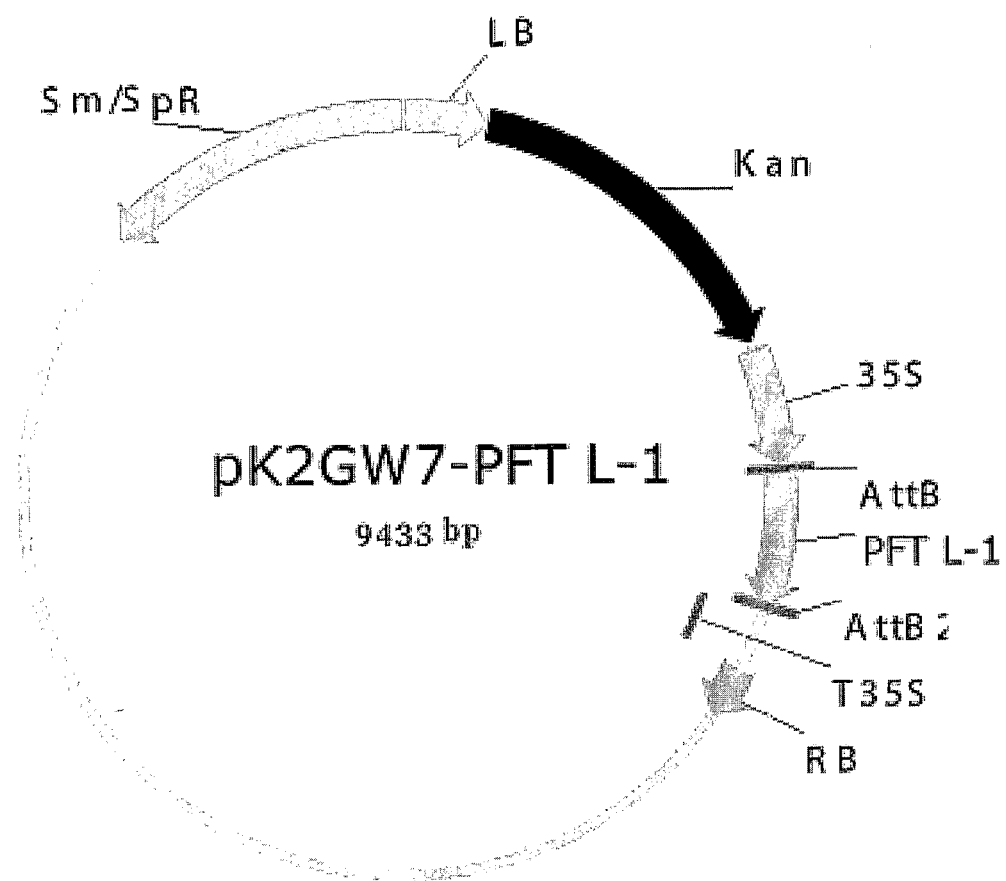
FIG. 4 shows the pK2GW7 35S::PFT L-1 vector.

The PFT L-1 coding sequence was amplified from cDNA originating from Populus tricocarpa male flowers with PCR using the primers "PFT L-1 forward": 5'ATGTCAAGGGA-CAGAGATCCTCTGAG3' (SECS ID NO:7) and "PFT L-1 reverse": 5'TTATGCGGTCCTACCACCAGAGC3' (SEQ ID NO:8). The forward primer contains an attB 1 site and the reverse primer an attB2 site. As template, cDNA originating from Populus tricocarpa male flowers was used. The 35S:: PFT L-1 vector was constructed by first recombining the PFT L-1 coding sequence into the entry vector pDONOR 201 using the GATEWAY™ system (Invitrogen), creating pDONR 201-PFT L-1, then moving PFT L-1 through another recombination reaction to the destination vector pK2GW7 to produce the final 35S:: PFT L-1 construct (FIG. 4). All cloning reactions were preformed according to the manufacturers instructions.

Hybrid aspen, Populus tremula L×P. tremuloides Michx clone T89 was transformed with pK2GW7 35S::PFT L-1 and shoots were generated as described (Nilsson et al. (1992) Transgene. Res 1 209-220 (1992)). All Populus plants were planted on soil (Hasselfors Garden AB, Sweden), daily watered and fertilized twice a week (Superba S, Supra Hydro AB, Landskrona, Sweden). The transgenic 35S:: PFT L-1 Populus plants were grown in greenhouse for 6 months under long day conditions. (16 h light, 8 h dark, 300 µE, 23° C.).

Flowers were observed to form in the transgenic Populus tremula×tremuloides at about 4 weeks after transformation. By comparison, the normal flowering time of Populus tremula×tremuloides is about 10-15 years.

Weaker expressing lines were generated, rooted and planted in a greenhouse. These plants were observed to form normal-looking inflorescences, so called 'catkins', and contain phenotypically normal flowers 2-6 months after transfer to soil.

Wild type flowers were collected from mature plants growing outdoors in spring and 35S:: PFT L-1 flowers after six months grown in soil. The flowers were fixated in 25 mM phosphate buffer pH 7.0, 3% Glutaraldehyde and dehydrated with ethanol ladder 50-95%. The dehydrated flowers were embedded in plastic (Schwarze and Fink 1998). 6 µM section were done and stained with aqueous toluidine-blue-O solution 0.05%.

$^{35}$S::LFY induces the production of single flowers instead of inflorescensces, and has detrimental effects on the general growth of the plant. 35S::PFT1 plants produced a much more normal flowering without detrimental growth effects.

Figure 7:
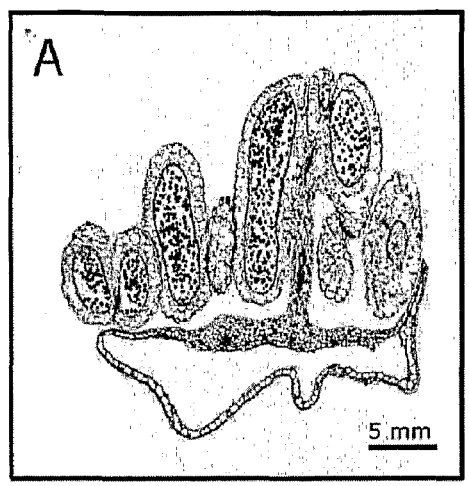
FIG. 7 shows (A) Wild type flowers with normal pollen and (B) $^{35}$S::PFT L-1 flowers with normal pollen.
Figure 7:
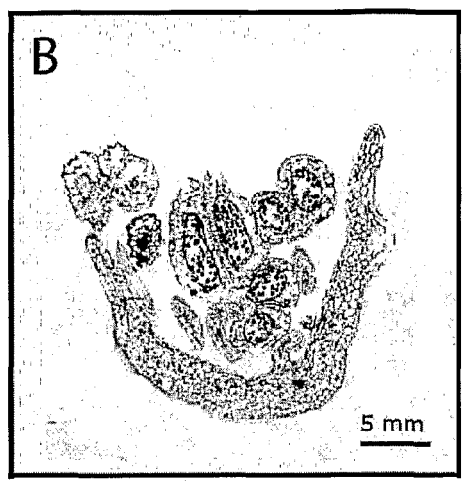

Early flowering and the production of inflorescences were observed in both male Populus tremula×tremuloides trees and in female Populus tremula trees. Male flowers formed on the transgenic trees appeared normal and produced pollen (FIG. 7). This demonstrates that the method works in both sexes of dioecious poplar trees and in different poplar species.

Note that the published 35S::FT constructs (pSKI083 and pSKI059) (WO99/53070: Kardailsky et al Science (1999) December 3; 286(5446):1962-5) were found to be ineffective in transforming Populus.

Inducible PFT Expression

Figure 3:
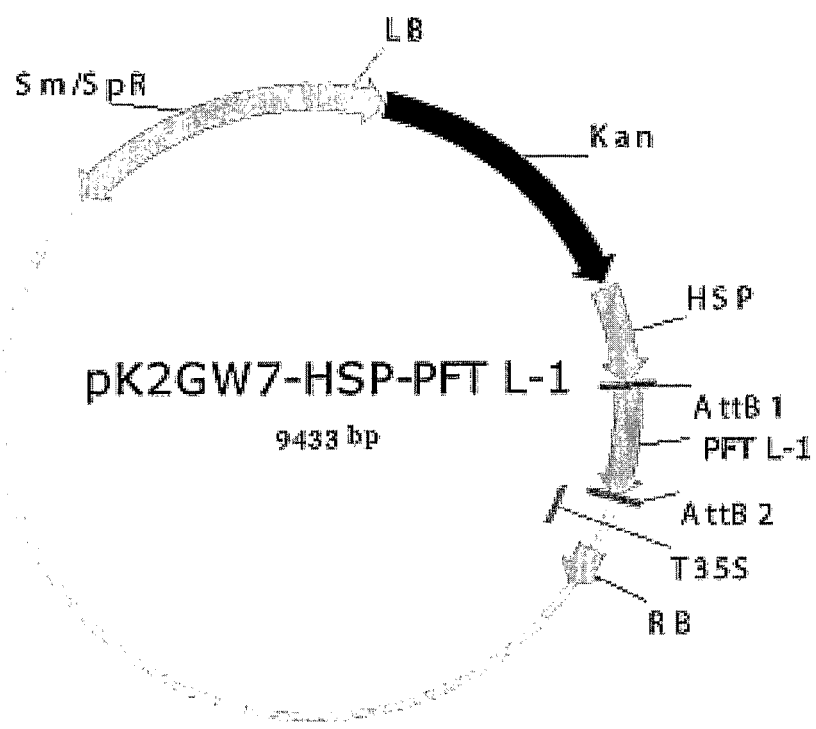
FIG. 3 shows the pK2GW7 HSP::PFT L-1 vector.

A heat-shock inducible PFT L-1 construct was made to see if the PFT L-1 gene could be inducibly expressed. The heat shock inducible promoter HSP (Severin K. and Schoffl F. 1990. *Plant Mol. Biol.* 15: 827-833) was inserted into pK2GW7 using Spe1 and Xba1 in front of the Gateway cassette creating pK2GW7-HSP. PFT L-1 was recombined into pDONR 201 creating pDONR 201-PFT L-1. This construct was recombined with the destination vector pK2GW7-HSP to create the final construct HSP::PFT1 (FIG. 3). The destination vector pK2GW7 is described in Karimi et al. (2002), Trends Plant Sci. 2002 May; 7(5):193-5.

Transgenic *Populus tremula×tremuloides* plants expressing the heat-shock inducible PFT L-1 construct were grown in long days (16 h light 8 h dark 300 µE 23° C.) for 6 weeks and then heated every day for 1 hour at 37° C. for three weeks.

Before the start of the heat-shock treatment, the transgenic plants were indistinguishable from wild-type controls, After three weeks of PFT L-1 induction, the transgenic plants started flowering and produced inflorescences. Once the inductive treatment is removed, the transgenic plants revert to vegetative growth, producing normal leaves and shoots.

Short Day Induced Growth Cessation

Transgenic *Populus tremula×tremuloides* expressing 35S::PFT L-1 were first grown under long day conditions (16 h light, 8 h dark, 300 µE, 23° C.) and then transferred to short days (8 h light, 16 h dark, 300 µE 23° C.). After 63 days in short days, plants were transferred to complete darkness at 5° C. for five days.

While wild-type plants were observed to respond to short days by producing terminal buds 32 days after being transferred to short day conditions and by shedding their leaves after 63 days in short days followed by 5 days in darkness, 35S::PFT L-1 expressing plants were observed to still be growing after 63 days in short days and five days in complete darkness at 5° C. without any signs of terminal bud set. At this point, the wild-type plants had already shed all their leaves and were in complete dormancy.

Figure 2:
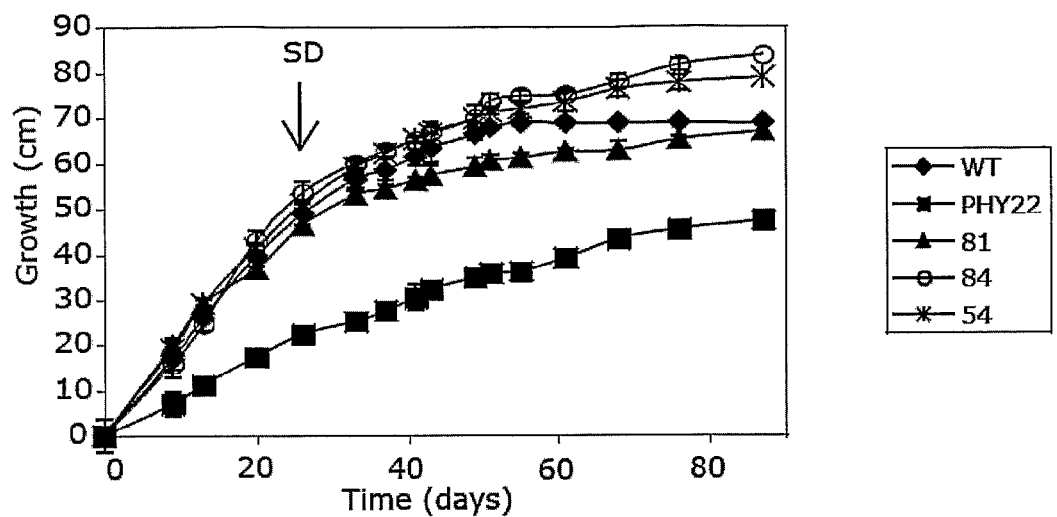

Growth was analyzed quantitatively by growing wild type, 35S::PFT-L1 and 35S::PHYA transgenic plants in long days (16 h light, 8 h dark 300 µE, 23° C.) for 23 days. Then, the plants were transferred to short days (8 h light, 16 h dark 300 µE, 23° C.) for another 63 days while growth was measured twice per week (FIG. 2).

The wild-type was observed to stop growing after 32 days in short-days and lost all the leaves 60 days after the shift, indicating growth cessation and bud-set. Neither 35S::PFT L-1 nor 35S::PHYA showed any response to the decrease in day length.

The expression of PFT1 in response to day length was followed in wild type plants.

Wild type *Populus tremula L×P. tremuloides* trees were grown in long day (LD) and short day (SD) conditions for 7 days before the sampling started the following morning. Mature leaves were collected every 4-hour for the next 2 days.

RNA was extracted from leaves using Total RNA Mini (BIORAD) according to their instructions. Poly (dT) cDNA synthesis was performed using the iScript cDNA Synthesis Kit (BIO-RAD) according to the manufacturers instructions. Quantification was performed on an iCycler iQ real-time PCR detection system (BIO-RAD) using the BIO-RAD iQ SYBR Green Supermix. PCR was carried out in 96 well optical reaction plates heated to 95° C. for 3 minutes followed by 45 cycles of 10S at 95° C., 30S at 55° C. and for 30S at 72° C. followed by a melting curve analysis starting at 54° C. to 95° C. with 0.5° C. per step to verify that the amplification was not caused by primer self-amplification but by a pure and common PCR product. For each quantification, conditions were 1>E>0.95 and r2>0.98, where E is the PCR efficiency and r2 corresponds to the correlation coefficient obtained by the standard curve. Tree replicate assays were performed independent of each other. Results were normalized to the expression of 18S ribosomal RNA. The primer used to detect PFT L-1 were 5'GAGAACTTCAACACCAGAGAC '3 (SEQ. ID NO:9) and 5'TCCATCCACCAGAGCCAG'3 (SEQ ID NO:10).

Figure 6:
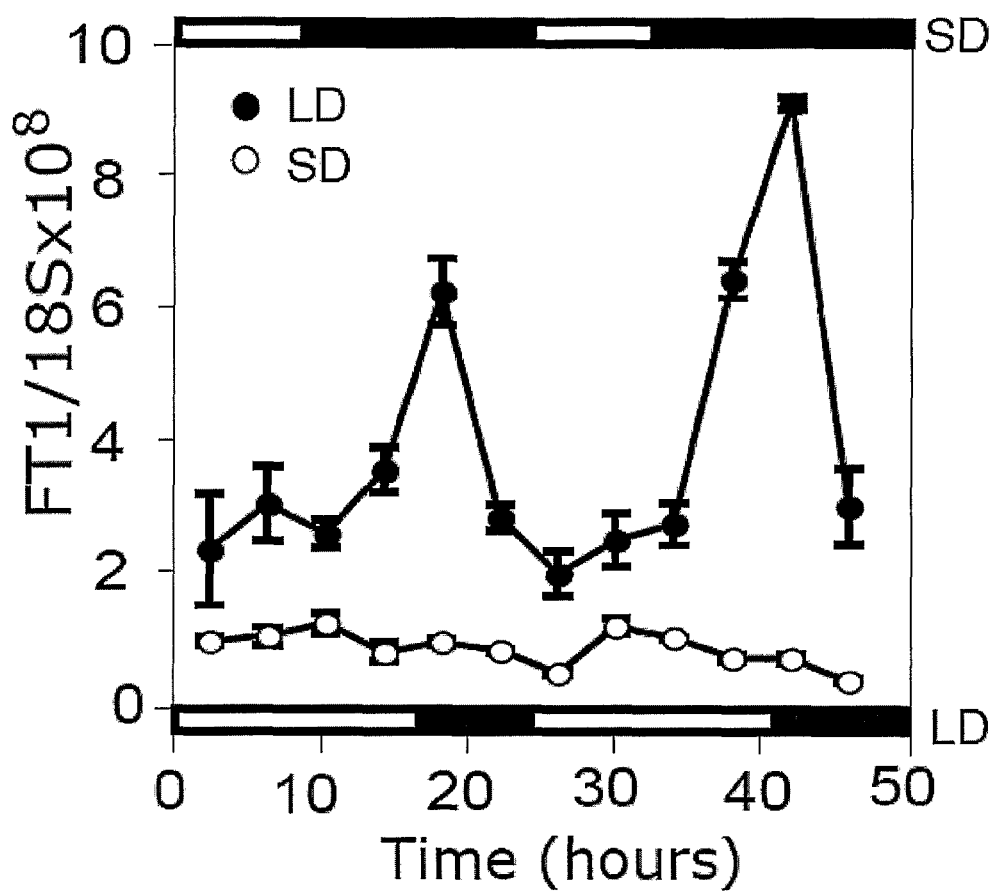
FIG. 6 shows the expression of PFT L-1 in response to day length in wild type plants

The results are shown in FIG. 6. Open circles represent long days (16 h light, 8 h dark 300 µE, 23° C.) and filled circles short days (8 h light, 16 h dark 300 µE, 23° C.).

In long days, PFT L-1 has a circadian oscillation pattern with a peak at the time the light goes off, but in short days PFT L-1 has no peak at lights off, leaving just low levels of expression (FIG. 6). Furthermore, after a shift from long days to short days, PFT1 expression in the wild-type was observed to dramatically decrease after about one week.

This data shows that, in addition to influencing flowering, PFT1 also represses short-day induced growth cessation.

Time to Bud Set in Wild-Type and PFT L-1 RNAi Poplar Lines

The critical day length of the wild type clone T89 is 15.5 h, which means that it can grow in 16 h day but not in 15 h. The effect of expression of PFT L-1 RNAi on short-day induced growth cessation was investigated.

Figure 8:
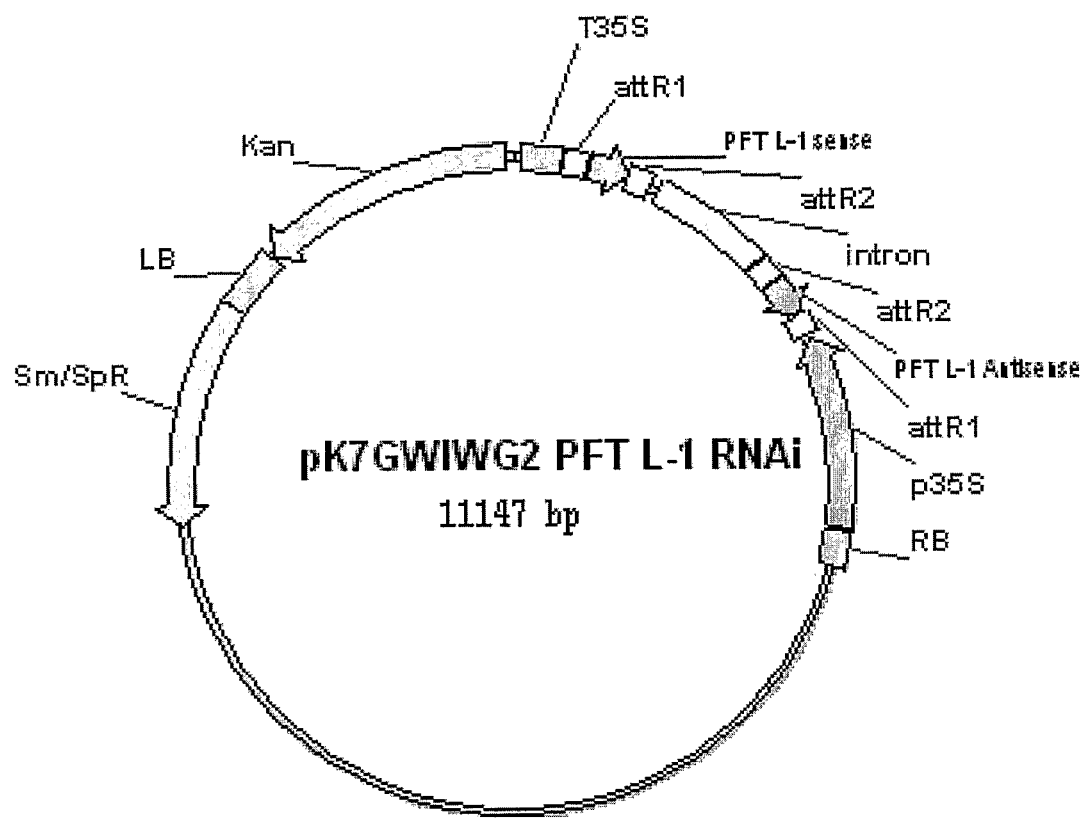
FIG. 8 shows the pKGWIWG2 PFT L-1 RNAi vector.

A region that showed high similarity to both PFT L-1 and PFT L-2 but not to other genes in the same gene family was PCR amplified with primer FOR 5'AGGTTGCCAAC-CAGCCTAGG 3' (SEQ ID NO:11) REV 5'AAGGTAAA-CAAACCTGTGGATCCC 3' (SEQ ID NO:12). The forward primer contains an attB1 site and the reverse primer contains an attB2 site. The 35S:: PFT L-1 RNAi vector was constructed by first recombining the PCR RNAi fragment into pDONR 201 with BP clonase and the by using LR clonase reaction creating the final pkgwiwg2 PFT L-1 RNAi fragment (FIG. 8). All cloning was performed according to the manufacturer's instructions.

Wild type T89 and PFT L-1 RNAi poplars were first grown in 18 hours light and then shifted to 15 h or 16 h light, while the bud set was scored. The results are shown in Table 1.

When the plants were shifted to 16 hours light (above the critical day length) for 3 weeks, one of PFT L-1 set bud after 3 weeks at 16 hours light, but none of the others. When the plants were shifted to 15 hours light (under the critical day length) for 2 weeks, 9 of the transgenic PFT L-1 RNAi lines showed a terminal bud but none of the wild type. This provides indication that a lack of PFT L-1 results in a shorter critical day length.

---

Sequence Listing

SEQ ID NO: 1

MSRDRDPLSVGRVIGDVLDPFTKSISLRVTYSSREVNNGCELKPSQVANQPRVDIGGEDLRTFYTLVM

VDPDAPSPSDPSLREYLHWLVTDIPATTGASFGHETVCYESPRPTMGIHRFVFVLFRQLGRQTVYAPG

WRQNFNTRDFAEVYNLGSPVAAVYFNCQRESGSGGRRR

Sequence Listing

SEQ ID NO: 2
ATGTCAAGGGACAGAGATCCTCTGAGCGTTGGCCGTGTTATAGGGGACGTGCTGGACCCCTTCACAAA
GTCTATCTCCCTCAGGGTCACTTACAGCTCCAGAGAGGTCAACAATGGTTGCGAGCTCAAGCCCTCTC
AGGTTGCCAACCAGCCTAGGGTTGATATTGGCGGGGAAGATCTAAGGACCTTCTACACTCTGGTTATG
GTGGACCCTGATGCACCCAGCCCAAGTGACCCCAGCCTAAGAGAATATTTGCATTGGTTGGTGACTGA
TATTCCAGCAACAACTGGGGCAAGCTTTGGCCATGAAACTGTGTGCTATGAGAGCCCGAGGCCGACAA
TGGGAATTCATCGGTTTGGTTTTCGTCTTGTTTCGGCAACTGGNGCAGGCAAACTGTGTATGCCCCTG
GGTGGCGCCAGAACTTCAACACCAGAGACTTTGCTGAGGTCTACAATCTTGGATCGCCAGTGGCTGCT
GTTTATTTCAACTGCCAGAGGGAGAGTGGCTCTGGTGGTAGGAGGCGATAA

SEQ ID NO: 3
MSINIRDPLIVSRVVGDVLDPFNRSITLKVTYGQREVTNGLDLRPSQVQNKPRVEIGGEDLRNFYTLV
MVDPDVPSPSNPHLREYLHWLVTDIPATTGTTFGNEIVCYENPSPTAGIHRVVFILFRQLGRQTVYAP
GWRQNFNTREFAEIYNLGLPVAAVFYNCQRESGCGGRRL

TABLE 1

| PFT L-1 RNAI | 3 weeks 16 H | 2 weeks 15 H | 4 weeks 15 H | 5 weeks 15 H |
|---|---|---|---|---|
| 2a | | | | |
| 3a | | | | |
| 4c | | | | |
| 4d | | | | |
| 4f | | | | |
| 5a | | | | |
| 6a | | | x | x |
| 6b | | x | x | x |
| 7a | | | | x |
| 9a | | x | x | x |
| 9b | | | | |
| 11a | | | | |
| 12a | | | | |
| 12b | | | | |
| 13a | | | | |
| 13b | | | | |
| 14a | | | | |
| 14b | | | | x |
| 15a | x | x | x | x |
| 15b | | | | x |
| 15c | | x | x | x |
| 15e | | | | |
| 16a | | x | x | x |
| 16b | | | | |
| 16C | | x | x | x |
| 16D | | x | x | x |
| 17a | | x | x | x |
| 17b | | | | |
| 17e | | x | x | x |
| 18a | | | | |
| 19a | | | | |
| 19d | | | | |
| 21d | | | | |
| WT | | | | x |
| WT | | | | |
| WT | | | | |
| WT | | | | |
| WT | | | | |

The invention claimed is:

1. A method of producing a transgenic hardwood tree comprising:
   a) incorporating a heterologous nucleic acid encoding a *Populus* Flowering locus T (PFT) polypeptide, or a vector comprising such a sequence, into a hardwood tree cell species by means of transformation, and;
   b) regenerating the transgenic hardwood tree from one or more transformed cells, wherein the PFT polypeptide comprises an amino acid sequence which shares greater than 80% sequence identity with the amino acid sequence of SEQ ID NO: 1, wherein the heterologous nucleic acid is operably linked to a promoter and is expressed in the transgenic hardwood tree, and wherein the transgenic hardwood tree shows early flowering relative to a control hardwood tree.

2. The method according to claim 1 wherein the hardwood tree is selected from the group consisting of *acacia, eucalyptus,* hornbeam, beech, mahogany, walnut, oak, ash, willow, hickory, birch, chestnut, poplar, alder, maple and sycamore.

3. The method according to claim 1 wherein the hardwood tree is a tree of the *Populus* or Salicaceae groups.

4. The method according to claim 1, wherein the hardwood tree is a fruit bearing tree.

5. The method according to claim 4 wherein the fruit bearing tree is selected from the group consisting of apple, plum, pear, banana, orange, kiwi, lemon, cherry, grapevine and fig.

6. A method of producing a transgenic hardwood tree having a desired trait comprising:
   (A) introducing into the cells of a male dioecious hardwood tree species having a desired trait a heterologous nucleic acid encoding a *Populus* Flowering locus T (PFT) polypeptide operably linked to a promoter, wherein expression of the heterologous nucleic acid induces early flowering, and; crossing said male tree with a female tree to produce progeny plants having the desired trait;
   (B) introducing into the cells of a female dioecious hardwood tree species having a desired trait a heterologous nucleic acid encoding a *Populus* Flowering locus T (PFT) polypeptide operably linked to a promoter, wherein expression of the heterologous nucleic acid induces early flowering, and; crossing said female hardwood tree with a male tree to produce progeny plants having the desired trait; or
   (C) introducing into the cells of a monocieous hardwood tree species having a desired trait a heterologous nucleic acid encoding a *Populus* Flowering locus T (PFT) polypeptide operably linked to a promoter, wherein expression of the heterologous nucleic acid induces early flowering, and; producing progeny from said hardwood tree which have the desired trait, wherein the PFT polypeptide comprises an amino acid sequence which shares greater than 80% sequence identity with the amino acid sequence of SEQ ID NO: 1.

7. The method according to claim 6 comprising selecting, from said progeny, hardwood trees which flower early and have the desired trait.

8. The method according to claim 7 comprising self-crossing said selected progeny to produce an inbred line.

9. The method according to claim 6 wherein the desired trait is selected from the group consisting of growth rate, size, form, timing of growth, seed germination, wood properties, fibre strength, fibre length, leaf characteristics, cone morphology, pest resistance, and capacity to withstand climatic stresses.

10. The method according to claim 1, wherein the PFT polypeptide comprises the amino acid sequence of SEQ ID NO: 1.

11. The method according to claim 1 wherein the heterologous nucleic acid comprises the nucleic acid sequence of SEQ ID NO: 2.

12. The method according to claim 1 wherein the promoter is inducible.

13. The method according to claim 12 wherein the promoter is the HSP promoter.

14. The method according to claim 12 wherein said inducible promoter is activated to express said heterologous nucleic acid such that said transgenic hardwood tree produces flower buds, the method further comprising:
  deactivating said inducible promoter to stop expression of said heterologous nucleic acid,
  causing or allowing the hardwood tree to deactivate growth and become dormant, and;
  causing or allowing the hardwood tree to reactivate growth, such that early flowering is induced from said flower buds.

15. A method of producing an early flowering transgenic hardwood tree comprising:
  incorporating a heterologous nucleic acid encoding a *Populus* Flowering locus T (PFT) polypeptide, or a vector comprising such a sequence, into a hardwood tree cell species by means of transformation, and;
  regenerating the transgenic hardwood tree from one or more transformed cells,
  wherein the PFT polypeptide comprises an amino acid sequence which shares greater than 95% sequence identity with the amino acid sequence of SEQ ID NO: 1, wherein the heterologous nucleic acid is operably linked to a promoter and is expressed in the transgenic hardwood tree, and wherein the transgenic hardwood tree shows early flowering relative to a control hardwood tree.

16. A method of producing an early flowering transgenic hardwood tree comprising:
  incorporating a heterologous nucleic acid encoding a *Populus* Flowering locus T (PFT) polypeptide, or a vector comprising such a sequence, into a hardwood tree cell species by means of transformation, and;
  regenerating the transgenic hardwood tree from one or more transformed cells,
  wherein the PFT polypeptide comprises an amino acid sequence which shares greater than 90% sequence identity with the amino acid sequence of SEQ ID NO: 1, wherein the heterologous nucleic acid is operably linked to a promoter and is expressed in the transgenic hardwood tree, and wherein the transgenic hardwood tree shows early flowering relative to a control hardwood tree.

* * * * *